United States Patent
Pudduck

(10) Patent No.: US 12,111,325 B2
(45) Date of Patent: Oct. 8, 2024

(54) ANALYTE DETECTION SYSTEM, AND METHODS OF USE RELATED THERETO

(71) Applicant: Siemens Healthcare Diagnostics Inc., Tarrytown, NY (US)

(72) Inventor: Christian Pudduck, Norfolk, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 819 days.

(21) Appl. No.: 17/268,185

(22) PCT Filed: Aug. 19, 2019

(86) PCT No.: PCT/US2019/047003
§ 371 (c)(1),
(2) Date: Feb. 12, 2021

(87) PCT Pub. No.: WO2020/046609
PCT Pub. Date: Mar. 5, 2020

(65) Prior Publication Data
US 2021/0302443 A1  Sep. 30, 2021

Related U.S. Application Data

(60) Provisional application No. 62/723,189, filed on Aug. 27, 2018.

(51) Int. Cl.
*G01N 33/72* (2006.01)
*G01N 21/31* (2006.01)
*G01N 27/27* (2006.01)

(52) U.S. Cl.
CPC ......... *G01N 33/726* (2013.01); *G01N 21/314* (2013.01); *G01N 27/27* (2013.01); *G01N 2021/3144* (2013.01)

(58) Field of Classification Search
CPC .... G01N 33/726; G01N 21/314; G01N 27/27; G01N 2021/3144; G01N 27/26; G01N 33/4925
See application file for complete search history.

(56) References Cited

U.S. PATENT DOCUMENTS 9,759,651 B2   9/2017  Sheppard, Jr. et al.
2006/0245793 A1  11/2006  Tatsumi et al.

FOREIGN PATENT DOCUMENTS

| EP | 1986007 A1 | 10/2008 |
| WO | 0005581 A1 | 2/2000 |
| WO | 2017108646 A1 | 6/2017 |
| WO | 2017165967 A1 | 10/2017 |

OTHER PUBLICATIONS

European Search Report and Written Opinion of European Application No. 19855826.4 dated Sep. 15, 2021.
International Search Report and Written Opinion of International Application No. PCT/US2019/047003 dated Nov. 1, 2019.

*Primary Examiner* — Jill A Warden
*Assistant Examiner* — Michael Paul Shimek

(57) ABSTRACT

Improved analyte detection system within a blood gas analyzer, the improved system comprising and/or consisting of at least one CO-oximetry system that is formed as an integrated, unitary structure(s) with an electrochemical sensor module, and methods of use related thereto.

14 Claims, 4 Drawing Sheets

ANALYTE DETECTION SYSTEM, AND METHODS OF USE RELATED THERETO

CROSS REFERENCE TO RELATED APPLICATIONS

Not Applicable.

STATEMENT REGARDING FEDERALLY SPONSORED RESEARCH OR DEVELOPMENT

Not Applicable.

TECHNICAL FIELD

The presently disclosed and/or claimed inventive concept(s) relates generally to non-limiting embodiments of an improved analyte detection system within a blood gas analyzer for the detection of analytes of interest present within a patient's liquid test sample, such as, by way of example only, a patient's whole blood sample. More specifically, the presently disclosed and/or claimed inventive concept(s) relates to non-limiting embodiments of an improved analyte detection system within a blood gas analyzer comprising and/or consisting of at least one electrochemical sensor module that is formed as a unitary structure(s) with, and not separately connected to, a CO-oximetry system for the detection of various species of hemoglobin which may be present in a patient's whole blood sample.

BACKGROUND

Some modern-day blood analyzers conduct CO-oximetric measurements via at least one CO-oximeter that measures the oxygen-carrying state of hemoglobin in a patient's liquid test sample, for instance, by way of example only, a patient's whole blood sample. In addition to traditional blood gas measurements conducted by blood gas analyzers (such as, by way of example only, determinations of the partial pressure of oxygen ($pO_2$), the partial pressure of carbon dioxide ($pCO_2$), pH (acidity), and the concentrations of sodium ($Na^+$), potassium ($K^+$), ionized calcium ($Ca^{++}$), chloride ($Cl^-$), glucose, and lactate), CO-oximeters utilize spectrophotometry to measure relative blood concentrations of various forms of hemoglobin present in the patient's blood sample. Such forms of hemoglobin include, by way of example only, oxygen-carrying hemoglobin or oxyhemoglobin ($O_2Hb$) (hemoglobin bound to molecular oxygen), non-oxygen-carrying normal hemoglobin or deoxyhemoglobin (HHb) (hemoglobin capable of binding to molecular oxygen), as well as dyshemoglobins, including, without limitation, carboxyhemoglobin (COHb) and methemoglobin (MetHb).

CO-oximetry is useful in establishing whether a patient is hypoxemic and/or hypoxic, identifying those patients who have an oxygen deficiency in the patient's tissue. Typically, CO-oximeters measure the absorption(s) of light passing through the patient's liquid test sample at varying wavelengths (ranging typically from 2-3 wavelengths to greater than or equal to several dozen wavelengths, including wavelengths present in the ultraviolet (UV), visible, and infrared (IR) spectra) to distinguish between the concentrations of oxyhemoglobin and deoxyhemoglobin. Thereafter, the oxyhemoglobin saturation is calculated (which represents the percentage of oxygenated hemoglobin ($O_2Hb$) compared to the total amount of available hemoglobin (Hb)). By measuring additional wavelengths of light absorption associated with a patient's liquid test sample, the CO-oximeter can establish the concentrations of additional hemoglobin species such as, by way of example only, carboxyhemoglobin, methemoglobin, and other hemoglobin moieties and light-absorbing species.

Traditional CO-oximetry systems are generally formed from separate modules that must be interconnected to one another to perform the various CO-oximetric measurements—for instance, a CO-oximetry optical cell(s) must be separately connected and secured to a sensor module. Such separately-connected, multi-component traditional systems, however, suffer from a number of disadvantages, such as, by way of example only: (1) increased volume of the patient's liquid test sample needed for the conductance of the CO-oximetry tests and measurements; (2) increased manufacturing costs associated with the high number of parts needed to form the CO-oximetry system; and (3) an increase in the likelihood of the CO-oximetry system's operational failure resulting from the individual or combined failure of the relatively large number of parts forming the system.

Accordingly, there is a need for an improved CO-oximetry system(s) (and methods of use and production related thereto) in which the functional parts of the system (such as, by way of example, the CO-oximetry optical cells and the sensor module(s)) are formed from a unitary structure and are not separately connected to one another. Such improved system overcomes the disadvantages associated with the traditional CO-oximetry systems—namely, the new and improved system(s), component(s), and/or methodology(-ies) at least allow for: (1) a decrease in the volume of patient's liquid test sample that is needed for the conductance of the CO-oximetric tests and measurements resulting from the decrease in the number of parts comprising the improved CO-oximetry system; (2) a reduction in CO-oximetry system complexity (and the likelihood of system failure) as the number of components comprising the improved CO-oximetry system is greatly reduced; and (3) a significant reduction in the manufacturing costs associated with the improved CO-oximetry system resulting from the decrease in parts needed for the functioning of the improved system. It is to such improved system(s), component(s), method(s) of manufacturing, and/or method(s) of use that the presently disclosed and/or claimed inventive concept(s) is directed.

DETAILED DESCRIPTION OF THE INVENTIVE CONCEPT(S)

Figure 1:
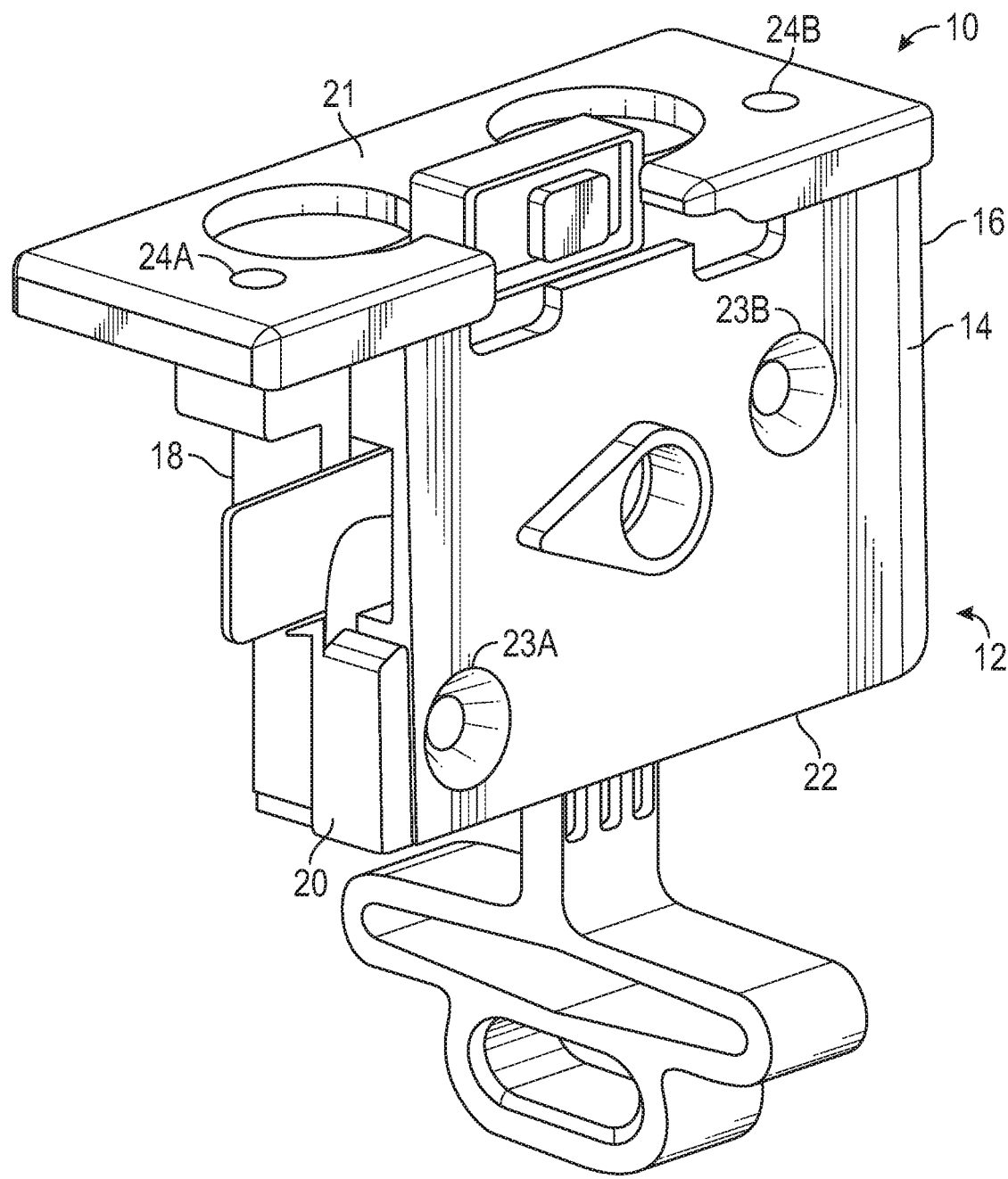
FIG. 1 is a perspective view illustrating one embodiment of an exterior of a CO-oximetry optical cell.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications and non-patent publications mentioned in the specification are indicative of the level of skill of those skilled in the art to which this presently disclosed and claimed inventive concept(s) pertains. All patents, published patent applications and non-patent publications referenced in any portion of this application are herein expressly incorporated by reference in their entirety to the same extent as if each individual patent or publication was specifically and individually indicated to be incorporated by reference.

All of the systems, articles, components, compositions, and/or methodologies disclosed and claimed herein can be made and executed without undue experimentation in light of the present disclosure. While the systems articles, components, compositions, and methodologies of the presently disclosed and/or claimed inventive concept(s) have been described in terms of preferred embodiments, it will be apparent to those of skill in the art that variations may be applied to the articles, compositions and/or methods and in the steps or in the sequence of steps of the methods described herein without departing from the concept, spirit and scope of the inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example, but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. In one non-limiting embodiment of the presently disclosed and/or claimed inventive concept(s), the patient's liquid test sample is whole blood. The volume(s) of liquid test sample utilized in accordance with the presently disclosed and/or claimed inventive concept(s) ranges from 0.1 microliter to about 250 microliters, or from about 1 microliter to about 245 microliters, or from about 5 microliters to about 240 microliters, or from about 10 microliters to about 230 microliters, or from about 20 microliters to about 220 microliters, or from about 30 microliters to about 210 microliters, or from about 40 microliters to about 200 microliters, or from about 50 microliters to about 190 microliters, or from about 60 microliters to about 180 microliters, or from about 70 microliters to about 170 microliters, or from about 80 microliters to about 160 microliters, or from about 90 microliters to about 150 microliters, or from about 100 microliters to about 140 microliters, or from about 110 microliters to about 130 microliters, or greater than or equal to about 120 microliters. In one non-limiting embodiment, the volume(s) of liquid test sample utilized in accordance with the presently disclosed and/or claimed inventive concept(s) is from about 40 microliters to about 80 microliters. In another non-limiting embodiment, the volume of liquid tets sample utilized in accordance with the presently disclosed and/or claimed inventive concept(s) is about 40 microliters to about 50 microliters.

The term "CO-oximeter" as used herein refers to a device that measures the oxygen carrying state of hemoglobin and other compounds in a blood specimen, such as, way of example only, a whole blood specimen, including measurements of total hemoglobin (tHb), $O_2Hb$, HHb, COHb, MetHb, and neonatal total bilirubin. In one non-limiting embodiment, the CO-oximeter utilizes a patient's arterial blood sample and multi-wavelength spectrophotometry (operating in the ultraviolet, visible, and/or infrared spectra) which quantitatively measures the absorbances of the various hemoglobin constituents present in the patient's whole blood sample.

The term "circuitry" as used herein shall be understood to mean analog and/or digital components, or one or more suitably programmed processors (e.g., microprocessors) and associated hardware and software, or hardwired logic. Also, "components" may perform one or more functions. The term "component," as used in the context of circuitry, may include hardware, such as a processor (e.g., microprocessor), an application specific integrated circuit (ASIC), field programmable gate array (FPGA), a combination of hardware and software, and/or the like. In one non-limiting embodiment, the term circuitry refers to electronic circuitry and components related thereto necessary for the presently disclosed and/or claimed CO-oximetry system to obtain quantitative measurements associated with a patient's liquid test sample, including, without limitation, a patient's whole blood sample, such as, by way of example only, spectrophotometric measurements related to the concentrations of various forms of hemoglobin present in a patient's liquid test sample.

The term "software" as used herein may include one or more computer readable instructions that, when executed or initiated by a user, cause the system component and/or instrument (such as, by way of example only, a spectrophotometer within a blood gas analyzer) to perform a specified function (including, without limitation, the measurement of concentrations of various forms of hemoglobin present in a patient's liquid test sample). It should be understood that the algorithms described herein may be stored on one or more non-transient memory. Exemplary non-transient memory may include random access memory, read only memory, flash memory, and/or the like. Such non-transient memory may be electrically-based, optically-based, and/or the like.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc. In one non-limiting embodiment of the presently disclosed and/or claimed inventive concept(s), the patient is a human patient.

Turning now to particular non-limiting embodiments, the presently disclosed and/or claimed inventive concept(s) relate to device(s), system(s), kit(s), component(s), and/or method(s) directed and/or related to an improved analyte detection system(s) within a blood gas analyzer (such as, by way of example only, a RAPIDPoint 500 Blood Gas Analyzer System and/or a RAPIDLab 1200 Blood Gas Analyzer System commercially offered for sale by Siemens Healthcare Diagnostics, Inc.) for the detection of analytes of interest which may be present within a patient's liquid test sample, such as, by way of example only, a patient's whole blood sample. More specifically, the presently disclosed and/or claimed inventive concept(s) relates to an improved analyte detection system within a blood gas analyzer, the improved analyte detection system comprising and/or consisting of at least one electrochemical sensor module and a CO-oximetry system, the at least one electrochemical sensor module and CO-oximetry system being formed as a unitary (i.e., not separately connected) structure(s) in or on a base for the performance of one or more analyte detection assays and/or measurements.

It is contemplated that virtually any reagent used in the fields of biological, chemical, or biochemical analyses and assays could be used in the devices, kits, components, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the devices, kits, components, and methods of the presently claimed and inventive concepts. A variety of assays for detecting analytes are well known in the art and include, but are not limited to, chemical assays, enzyme inhibition assays, antibody stains, latex agglutination, latex agglutination and as, inhibition immunoassays, such radioimmunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2). In one non-limiting embodiment of the presently disclosed and/or claimed inventive concept(s), the method of detection comprises the use of multi-wavelength spectrophotometry for the measurement of the concentration(s) of various forms of hemoglobin which may be present in a patient's whole blood sample.

Assays, including, but not limited to, immunoassays, nucleic acid capture assays, lipid-based assays, chemical-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin (including, without limitation, oxyhemoglobin ($O_2Hb$), deoxyhemoglobin (HHb), carboxyhemoglobin (COHb), methemoglobin (MetHb), and total amount of available hemoglobin (Hb)), myoglobin, $\alpha$-1-microglobin, immunoglobins, enzymes, proteins, glycoproteins, protease inhibitors, drugs, cytokines, creatinine, and glucose. The device(s), kit(s), component(s), and method(s) disclosed and/or claimed herein may be used for the analysis of any liquid test sample, including, without limitation, whole blood, plasma, serum, or urine. In one non-limiting embodiment, the liquid test sample is whole blood and the diagnostic assay performed is a blood gas and/or CO-oximetric assay panel on said whole blood in accordance with the presently disclosed and/or claimed inventive concept(s).

Referring now to the Figures, and in particular, to FIG. 1, shown therein is a perspective view illustrating an embodiment of an exterior portion of an embodiment of a CO-oximetry optical cell 10.

As shown in FIG. 1, the exterior portion of the CO-oximetry optical cell 10 comprises an optical cell body 12, the optical cell body 12 comprising a first thermal cover 14, a first side 16, a second thermal cover 18, a second side 20, a first end 21, and a second end 22. When connected (as shown in FIG. 1), the first thermal cover 14 and the second thermal cover 18 form the optical cell body 12. The optical cell body 12 is substantially rectangular in shape and the interior space of the optical cell body 12 is hollow and houses the internal, functional components (shown in greater detail in FIG. 2) further comprising the CO-oximetry optical cell 10. The first thermal cover 14 and the second thermal cover are secured to one another by a first cover screw and second cover screw (shown in FIG. 2) which fit through thermal cover securement holes 23A and 23B, respectively, thereby securing the first thermal cover 14 and the second thermal cover 18 to one another. The internal, functional components of the CO-oximetry optical cell 10 (shown in greater detail in FIG. 2) are incorporated into the optical cell body 12 prior to the securement of the first thermal cover 14 to the second thermal cover 18. The first side 16 and the second side 20 of the optical cell body 12 are formed via the securement of the first thermal cover 14 and the second thermal cover 18 to one another. The first side 16 and second side 20 are oriented substantially perpendicular to the first end 21 and the second end 22 of the optical cell body 12, the first side 16 and second side 20 extending longitudinally between the top side 21 and the bottom side 22. As shown in FIG. 1, the functional components of the CO-oximetry optical cell 10 are primarily contained within the optical cell body 12; however, the optical cell body 12 is configured such that the functional components of the CO-oximetry optical cell 10 may extend through the first side 16, the second side 20, the first end 21, and/or the second end 22.

The CO-oximetry optical cell 10 requires separate attachment to an electrochemical sensor module (shown in greater detail in FIG. 2) in order to provide functional analyte detection and blood gas analysis of a patient's liquid test sample. The CO-oximetry optical cell 10 is secured via a first securement screw and a second securement screw (shown in FIG. 2) which fit through optical cell body securement holes 24A and 24B to thereby secure the prior art CO-oximetry optical cell 10 to the sensor module/cartridge.

Figure 2:
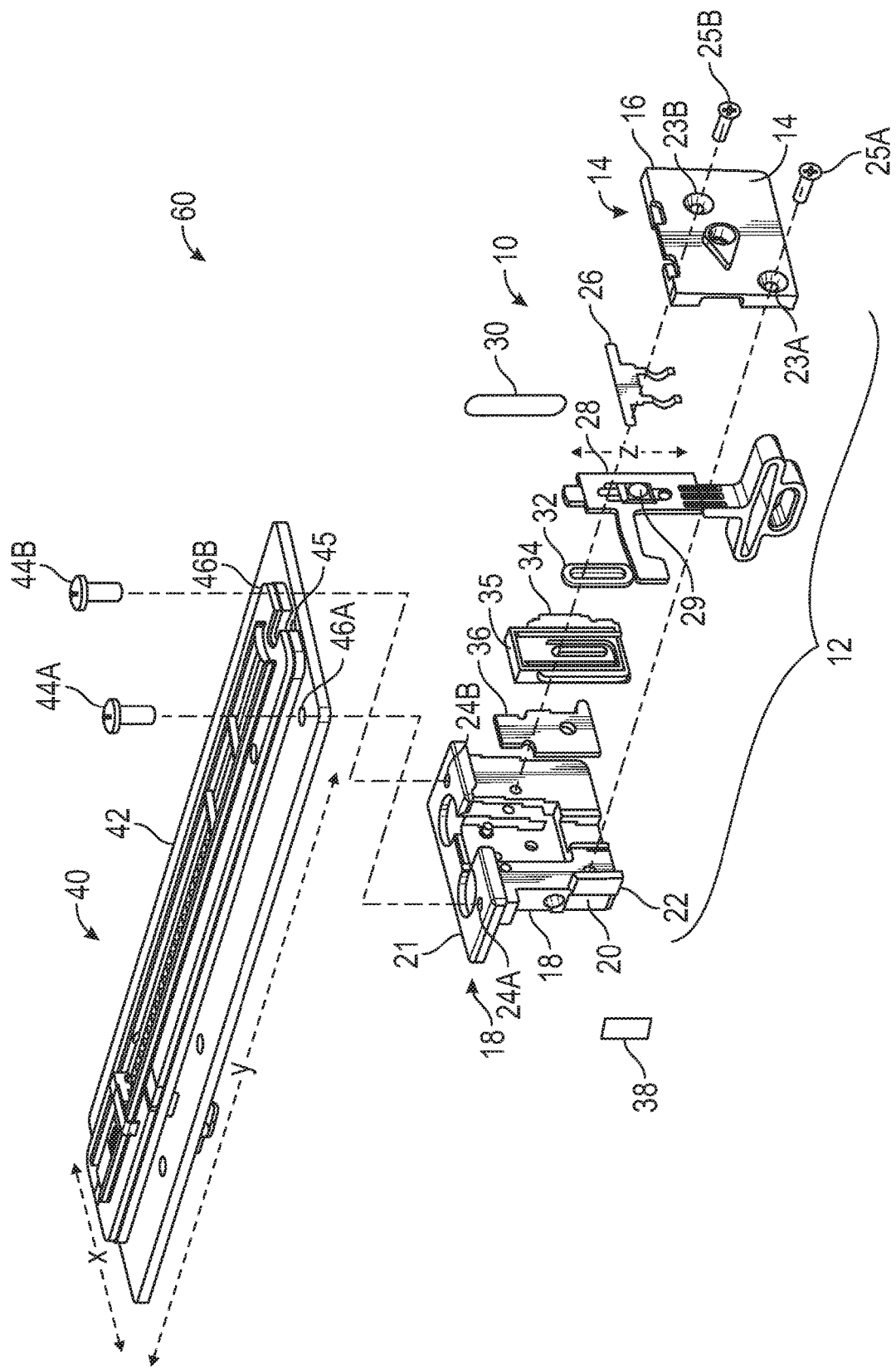
FIG. 2 is a detailed, exploded perspective view illustrating one embodiment of a CO-oximetry system comprising the prior art CO-oximetry optical cell of FIG. 1 separately attached and secured to an electrochemical sensor module.

Referring now to FIG. 2, shown therein is a detailed, exploded perspective view illustrating an analyte detection system 60 comprising the CO-oximetry optical cell 10 of FIG. 1 which is separately attached to an electrochemical sensor module 40.

The description of the CO-oximetry optical cell 10 with respect to FIG. 1 is deemed wholly applicable to the CO-oximetry cell 10 shown in FIG. 2. Accordingly, for purposes of brevity, only the structural and functional differences of the CO-oximetry optical cell 10 not shown in or discussed with respect to FIG. 1 will be discussed with respect to FIG. 2.

As shown in FIG. 2, the CO-oximetry optical cell 10 of the analyte detection system 60 further comprises additional functional components located within the optical cell body 12 between the first thermal cover 14 and the second thermal cover 18. These additional functional components facilitate the conductance of at least one CO-oximetric assay on a patient's liquid test sample and include, but are not limited to: a spring 26; a shunt 28 comprising an optical measurement zone 29; a label 30; a first gasket 32 sealing the junction between the shunt 28 and the sample chamber 34; a sample chamber 34 wherein the patient's liquid test sample is subjected to various spectrophotometric measurements; a second gasket 36 sealing the junction between the sample chamber 34 and the second thermal cover 18; and a heater chip 38 integrated onto and connected to the second side 20 of the body 12 of the CO-oximetry optical cell 10 for the control and/or adjustment of the temperature(s) related to the CO-oximetric measurement(s). The shunt 28, upon receiving a portion of the patient's liquid test sample (such as, by way of example, whole blood), moves longitudinally in the z-plane (shown as bidirectional arrow z in FIG. 2) thereby thinning and/or slicing the patient's liquid test sample, and depositing a thin layer (i.e., a layer having a thickness of from about 80 microns to about 160 microns) of the patient's liquid test sample on a surface of the optical measurement zone 29. Once deposited, the thinned sample is interrogated by at least one optical source for the conductance of at least one CO-oximetric assay.

The analyte detection system 60 further comprises a separate electrochemical sensor module 40, the electrochemical sensor module 40 comprising a base 42 which houses any reagent(s), sensor(s), hemolyzer(s), separation devices, and/or any other components necessary for the conductance of electrochemical and/or optical assays and/or measurements.

While not specifically shown in FIG. 2, the analyte detection system 60 may further comprise components necessary for the functioning of both the CO-oximetry optical cell 10 and the electrochemical sensor module 40 such as, by way of example, heaters, thermally-controlled connection tubing, and/or sample position detectors.

As shown in FIG. 2, the analyte detection system 60 is formed via the connection of the separate CO-oximetry optical cell 10 to the separate electrochemical sensor module 40. The CO-oximetry optical cell 10 is separately secured to the electrochemical sensor module 40 via a first securement screw 44A and a second securement screw 44B. The first securement screw 44A passes through a first securement hole 46A on the base 42 of the electrochemical sensor module 40 and through the first CO-oximetry optical cell body securement hole 24A. Likewise, the second securement screw 44B passes through a second securement hole 46B on the base 42 of the electrochemical sensor module 40 and through the second CO-oximetry optical cell body securement hole 24B. Accordingly, the separate CO-oximetry optical cell 10 is secured to the separate electrochemical sensor module 40 via the first securement screw 44A and the second securement screw 44B thereby forming the analyte detection system 60. Once formed, the patient's liquid test sample is introduced into the electrochemical sensor module 40 and travels in the x and y planes (as shown by directional arrows x and y in FIG. 2) through channels (not shown) therein to allow for electrochemical analysis of the patient's liquid test sample. After flowing through the electrochemical sensor module 40, the patient's liquid test sample exits the electrochemical sensor module 40 via electrochemical sensor module exit port 45 and drops into the CO-oximetry sample chamber 34 via CO-oximetry sample chamber entry port 35. Once within the CO-oximetry sample chamber 34, the patient's liquid test sample travels through the various components of the CO-oximetry optical cell 10 for the conductance of one or more optical assays and/or measurements.

Figure 3:
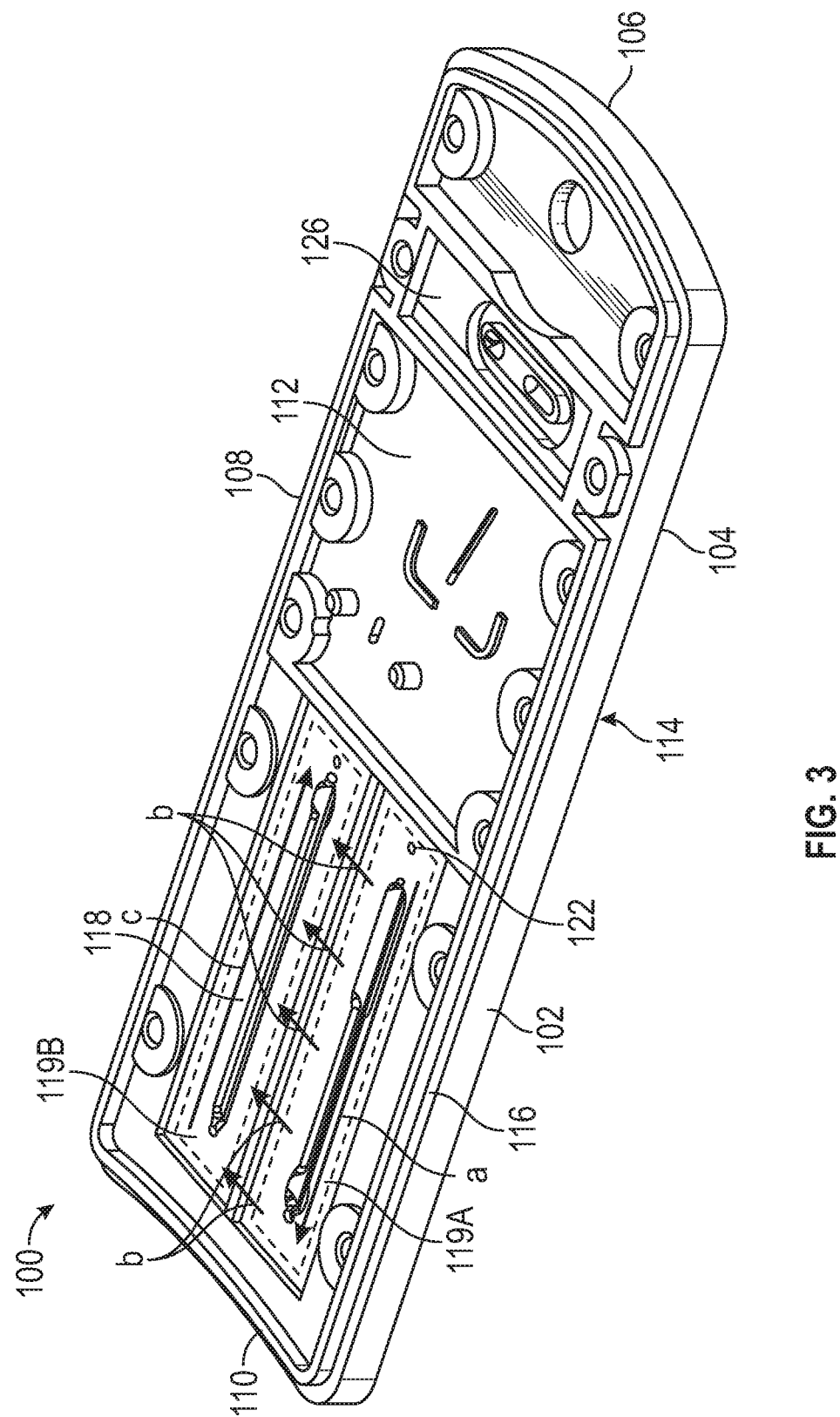
FIG. 3 is a detailed, perspective view of a non-limiting embodiment of an improved and integrated system platform constructed in accordance with the presently disclosed and/or claimed inventive concept(s).

Referring now to FIG. 3, shown therein is a detailed, perspective view of a non-limiting embodiment of an improved analyte detection system platform 100 constructed in accordance with the presently disclosed and/or claimed inventive concept(s). As described in further detail hereinbelow, the analyte detection system platform 100 comprises a base 102 that houses various components for conducting both chemical (such as electro-chemical) assays and CO-oximetric assays on a patient's single liquid test sample.

As shown in FIG. 3, in one non-limiting embodiment, the base 102 comprises and/or consists of a first side 104, a first end 106, a second side 108, a second end 110, a top surface 112, and a bottom surface 114. While shown in FIG. 3 as being substantially rectangular in shape, a person having ordinary skill in the art should readily appreciate that the base 102 can be any shape capable of accomplishing the presently disclosed and/or claimed inventive concept(s), including, without limitation, circular, triangular, square, pentagonal, hexagonal, heptagonal, octagonal, nonagonal, decagonal, or any polygonal shape. In one non-limiting embodiment, the base 102 is constructed of a transparent and/or translucent material(s), including, without limitation, synthetic and/or naturally-occurring or derived polymers (both organic and/or inorganic), such as, by way of example only, thermoplastic polymer(s), thermoset polymer(s), elastomer(s), and/or synthetic fiber(s) such as low-density polyethylene, high density polyethylene, polystyrene, polyvinylchloride, styrene butadiene, polyacrylics, polyvinyl acetate, acrylic, acrylic acid, and acrylate polymers, and combinations thereof.

Figure 4:
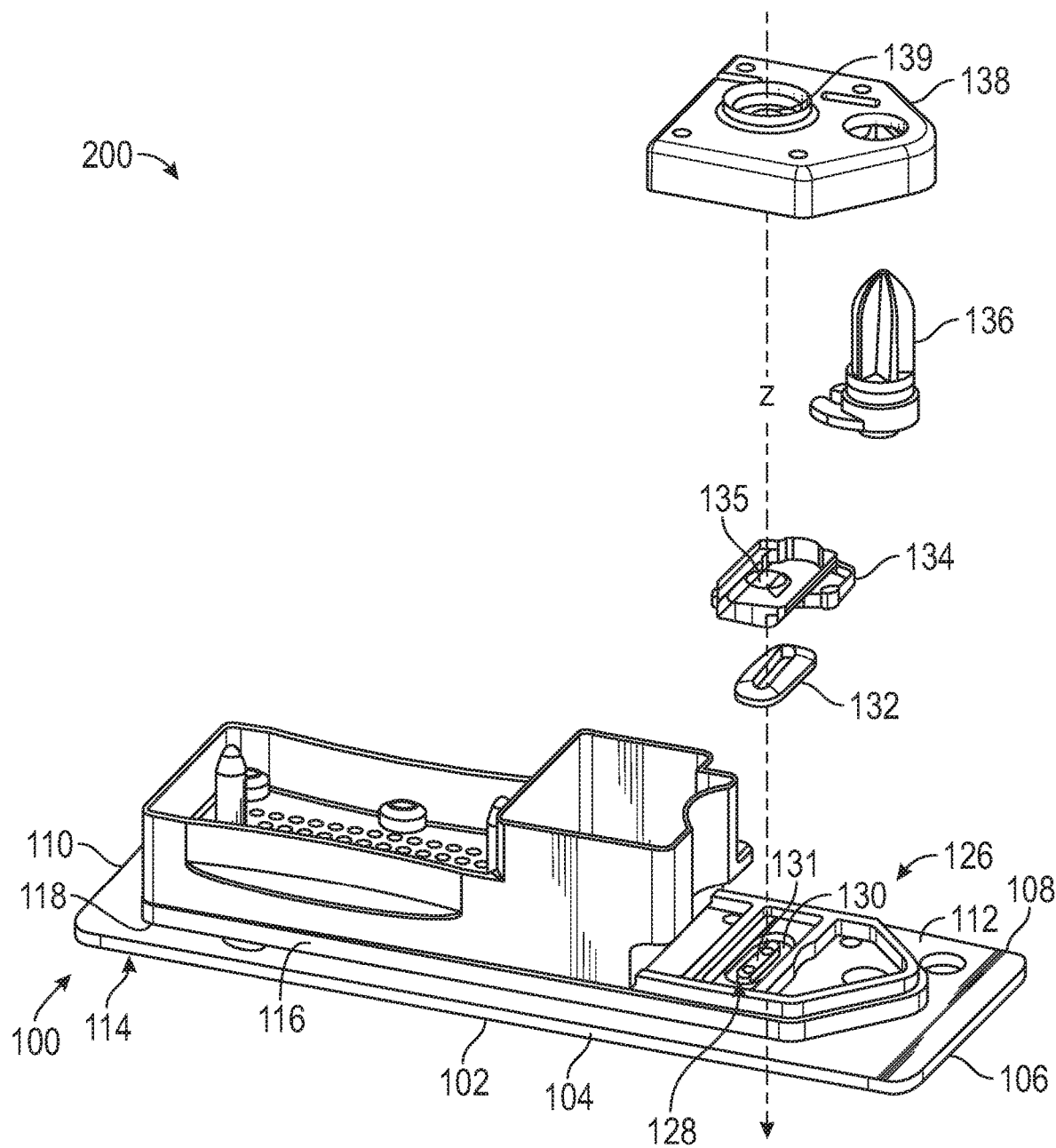
FIG. 4 is a detailed, exploded perspective view of an improved, integrated analyte detection system constructed in accordance with the presently disclosed and/or claimed inventive concept(s).

In one non-limiting embodiment of the presently disclosed and/or claimed inventive concept(s), the base 102 further serves as a unitary substrate for an integrated analyte detection system which comprises and/or consists of CO-oximetry and electrochemical systems (shown in greater detail in FIG. 4). In one non-limiting embodiment, the base 102 further comprises a base perimeter ridge 116 that extends substantially around the entire perimeter of the base 102 on the top surface 112 of the base 102. The base perimeter ridge 116 allows and/or facilitates the securement of additional components (shown in greater detail in FIG. 4) to the base 102 of the improved analyte detection system platform 100 for the conductance of chemical (including, without limitation, electrochemical) and/or CO-oximetry assays. While FIG. 3 depicts the base perimeter ridge 116 as being formed from and/or in the base 102 as a unitary structure, such as, by way of example only, etched into and/or constructed from the top surface 112 of the base 102, a person having ordinary skill in the art should readily appreciate that the base perimeter ridge 116 may be separate from and affixed to, by way of example only, the top surface 112 of the base 102. Alternatively, the base 102 may not include the base perimeter ridge 116 and the additional components for conducting electrochemical and/or CO-oximetry assays may be connected and secured to the base 102 via any methodology(-ies) and via any structure(s) commonly known in the art.

As shown in FIG. 3, in one non-limiting embodiment, the base 102 further comprises an electrochemical assay portion 118, a liquid test sample inlet 122, and a CO-oximetry assay portion 126.

In one non-limiting embodiment (and as shown in FIG. 3), the electrochemical assay portion 118 of the base 102 comprises a first electrochemical sensor substrate 119A and a second electrochemical sensor substrate 119B; however, it should be understood to a person having ordinary skill in the art that the base 102 may comprise any number of electrochemical sensor substrates including, without limitation, 1, 2, 3, 4, 5, 6, 7, 8, 9, or greater than or equal to 10 electrochemical sensor substrates (the number of electrochemical sensor substrates directly corresponding to the number of electrochemical sensors). The first electrochemical sensor substrate 119A and the second electrochemical sensor substrate 119B may be the same or different both in configuration and the electrochemical assays/measurements performed. In addition, the first electrochemical sensor substrate 119A and the second electrochemical sensor substrate 119B, while shown in FIG. 3 as being located on the top surface 112 of the base 102, they may be located on the same or different sides in order to accomplish the presently disclosed and/or claimed inventive concept(s). For instance, the first electrochemical sensor substrate 119A may be located on the top surface 112 of the base 102 and the second electrochemical sensor substrate 119B may be located on the bottom surface 114 of base 102; alternatively, the first electrochemical sensor substrate 119A and the second electrochemical sensor substrate 119B may both be located on the bottom surface 114 of the base 102. The first electrochemical sensor substrate 119A serves as a base for a first electrochemical sensor (not shown) that conducts at least one electrochemical assay and/or measurement upon receipt of the patient's liquid test sample. Similarly, the second electrochemical sensor substrate 119B serves as a base for a second electrochemical sensor (not shown) that conducts at least one electrochemical assay and/or measurement upon receipt of the patient's liquid test sample.

The liquid test sample inlet 122 receives a patient's liquid test sample which may be disposed in the liquid test sample inlet 122 via manual or automated methods, including, without limitation, via injection from pipette(s), vacutainer(s), and/or capillary(-ies). Once disposed in the liquid test sample inlet 122, the patient's liquid test sample flows through at least one channel, one, some, or all of which may be microchannels (not shown), contained within the base 102 to thereby distribute (for instance, via capillary action or via applied pressure diffusion) the patient's liquid test sample (for instance, whole blood) to the electrochemical assay portion 118 and the CO-oximetry assay portion 126 of the base 102.

In one non-limiting embodiment, the patient's liquid test sample (such as, by way of example only, whole blood) is introduced into the liquid test sample inlet 122 wherein the patient's liquid test sample flows through at least one channel (not shown) across the first electrochemical sensor (not shown) in accordance with directional arrow a for the conductance of at least one electrochemical assay(s) and/or measurement(s). After (or simultaneously therewith) the patient's liquid test sample flows across the first electrochemical sensor, the sample flows through at least one channel to the second electrochemical sensor (not shown) in accordance with directional arrows b. Thereafter, the patient's liquid test sample flows through at least one channel (not shown) across the second electrochemical sensor (not shown) in accordance with directional arrow c for the conductance of at least electrochemical assay(s) and/or measurement(s). Following the conductance of the electrochemical assay(s) within the electrochemical assay portion 118, the patient's liquid test sample flows through at least one channel (not shown) in accordance with directional arrow d into the CO-oximetry assay portion 126 of the base 102 for the conductance of at least one CO-oximetric and/or optical assay(s) and/or measurement(s). While the flow of the patient's liquid test sample has been described herein as first flowing through the electrochemical assay portion 118 prior to flowing through and engaging with the CO-oximetric assay portion 126, a person having ordinary skill in the art should readily appreciate that the flow pattern can be modified and still accomplish the presently disclosed and/or claimed inventive concept(s). For instance, by way of example only, upon being introduced into the base 102 via the liquid test sample inlet 122, the patient's liquid test sample may first pass through the CO-oximetric assay portion 126 prior to passing through and engaging with the electrochemical assay portion 118. Additionally, the patient's liquid test sample may simultaneously pass through and engage with both the electrochemical assay portion 118 and the CO-oximetric assay portion 126 of the base 102 upon being introduced into the base 102 via liquid test sample inlet 122. As shown in FIG. 3, the patient's liquid test sample flows through base 102 which serves as a unitary structure that fully integrates the previously separate electrochemical and CO-oximetric/optical components of an analyte detection system.

As shown in FIG. 3 (and FIG. 4), the analyte detection system platform 100 comprises a base 102 that forms a unitary structure into (or onto) which an electrochemical assay portion 118 and CO-oximetry assay portion 126 are integrated. As shown in FIG. 4, in one non-limiting embodiment of the presently disclosed and/or claimed inventive concept(s), the electrochemical assay portion 118 and the CO-oximetry assay portion 126 are both integrated into or onto the top surface 112 of the base 102 of the analyte detection system platform 100; however, a person having ordinary skill in the should readily appreciate that the electrochemical assay portion 118 (and its related components as discussed elsewhere herein) and the CO-oximetry assay portion 126 (and it related components as discussed elsewhere herein) may be located on the same or different surfaces of the base 102 in order to accomplish the objectives of the presently disclosed and/or claimed inventive concept(s).

Referring now to FIG. 4, shown therein is a non-limiting embodiment of an improved, integrated analyte detection system 200. The improved, integrated analyte detection system 200 comprises the analyte detection system platform 100 depicted in FIG. 3 (as well as additional components discussed in greater detail herein). The description of the analyte detection system platform 100 with respect to FIG. 3 is deemed wholly applicable to the analyte detection system platform 100 shown in FIG. 4. Accordingly, for purposes of brevity, only the structural and functional differences (and/or additional components thereof) of the analyte detection system platform 100 not shown in or discussed with respect to FIG. 3 will be discussed with respect to FIG. 4.

In one non-limiting embodiment, the CO-oximetry assay portion 126 of the base 102 of the analyte detection system platform 100 comprises a CO-oximetry sensor module 128 which is located on the top portion 112 of the base 102 of the analyte detection system platform 100.

The CO-oximetry sensor module 128 comprises a sample chamber 130 that receives and holds the patient's liquid test sample from the channels (not shown and previously discussed) connecting the CO-oximetry assay portion 126 to the electrochemical assay portion 118 of the base 102. The sample chamber 130 further comprises a transparent and/or translucent optical measurement surface 131 that receives a portion of the patient's liquid test sample and, upon optical interrogation, provides CO-oximetric and/or optical analyses and/or measurement(s) of the patient's liquid test sample.

Once the patient's liquid test sample is disposed within the sample holder 130, the patient's liquid test sample is processed and prepared by additional components of the CO-oximetry sensor module 128 for CO-oximetric/optical analysis. Such additional components of the CO-oximetry sensor module 128 may include, but not be limited to: at least one gasket 132 to seal any junction(s) between sample holder 130 and shunt 134; a shunt 134 which engages the patient's liquid test sample (for instance, whole blood sample) within the sample holder 130 and reduces the thickness of the patient's liquid test sample (for instance, via a slicing motion occurring in the x-plane (i.e., back and forth between the first side 104 and the second side of the base 102) and/or the y-plane (i.e., back and forth between the first end 106 and the second end 110 of the base 102) before transferring the thinned sample to the optical measurement surface 131 for performance of CO-oximetry assay(s) and analysis/measurements; an actuator 136 for operating the shunt 134; and/or an optical cell cover 138 for covering the improved CO-oximetry assay portion 126, the cover 138 being permanently or selectively affixed to the base 102. The shunt 134 of the presently disclosed and/or claimed inventive concept(s) operates in multiple positions depending on the task being performed by the shunt 134. For instance, in one non-limiting embodiment, the shunt 134 is in an operable, slicing position/orientation that slices/thins the patient's liquid test sample before depositing the thinned sample (the sample thickness ranging from about 80 microns to about 160 microns) on the optical measurement surface 131 of the sample chamber 130. Following the thinning of the patient's liquid test sample, the shunt 134 reorients in a "wash-out" position that facilitates the removal of the patient's liquid test sample from the optical measurement surface 131 for additional testing of patients' liquid test samples.

As shown in FIG. 4, the patient's liquid test sample is interrogated by a light source (not shown) on the optical measurement surface 131 of the sample holder 130 of the CO-oximetry sensor module 128. The optical beam from the light source travels in a direction substantially perpendicular to the base 102 along the directional axis labeled z. In so doing, the optical beam from the light source passes through optical window 139 of the cover 138, through optical window 135 of the shunt 134, through an opening of the gasket 132, and onto and through the optical measurement surface 131 of the sample chamber 130. The patient's liquid test sample (subsequently deposited thereon after being thinned by the shunt 134) is accordingly interrogated by the optical beam of the light source on the optical measurement surface 131 and CO-oximetric/optical assay(s) and/or measurement(s) are performed and collected.

The electrochemical assay portion 118 and the CO-oximetry assay portion 126 of the improved analyte detection system 200 utilize the same base 102, wherein each component is affixed and/or secured to or formed from at least one portion the base 102 (such as, by way of example only, the top portion 112 of the base 102) while remaining in functional communication with each other to perform various electrochemical and/or CO-oximetric/optical assays and measurements. Accordingly, any duplicitous/redundant parts and/or parts utilized for the sealing and/or securement of the CO-oximetry optical cell 10 and the electrochemical sensor module 40 to one another are eliminated in the presently disclosed and/or claimed inventive concept(s). In addition, the analyte detection system's 200 complexity is significantly reduced over that of previous systems (such as, the analyte detection system 60 shown in FIG. 2) as the number of parts in the presently disclosed and/or claimed inventive concept(s) is greatly reduced. For instance, by way of example only, parts related to the sealing and securement of the CO-oximetry optical cell 126 to the electrochemical sensor module 118, as well as separate heaters, thermally-controlled connection tubing, and/or sample position detectors, are not utilized by (or necessary to) the construction and/or functioning of the presently disclosed and/or claimed inventive concept(s). Accordingly, the advantages associated with the reduction in overall system complexity in accordance with the presently disclosed and/or claimed inventive concept(s) include, but are not limited to: (1) the cost(s) associated with the production and manufacturing of the improved analyte detection system 200 is greatly reduced as compared to that of previous systems; (2) the reliability and performance of the improved analyte detection system 200 is improved over that of the more-complex previous systems; (3) the volume of the patient's liquid test sample needed to conduct the various electrochemical and co-oximetric/optical assays contemplated by the presently disclosed and/or claimed inventive concept(s) is similarly reduced; and (4) due to the integration of the electrochemical assay portion 118 and the CO-oximetric assay portion 126 on the same base 102, removal and replacement of the improved analyte detection system 200 within a blood gas analyzer is rendered easier and more efficient.

Non-Limiting Examples of the Inventive Concept(s)

An improved analyte detection system platform for conducting electrochemical and CO-oximetric assays, the platform comprising: a base, the base comprising at least one side, a top surface, and a bottom surface, the base further comprising: a liquid test sample inlet for receiving a patient's liquid test sample, the liquid test sample inlet being located on the top portion of the base; a plurality of microchannels located within the base and in fluid communication with the liquid test sample inlet, the plurality of microchannels being located between the top surface and bottom surface of the base; an electrochemical assay portion; and a CO-oximetry assay portion, wherein the chemical assay portion and the CO-oximetry assay portion are in fluid communication with and connected via the plurality of microchannels.

The improved analyte detection system platform, wherein the patient's liquid test sample is whole blood.

The improved analyte detection system platform, wherein the electrochemical assay portion and the CO-oximetry assay portion are formed from and located on a same surface of the base.

The improved analyte detection system platform, wherein the electrochemical assay portion and the CO-oximetry assay portion are located on a portion of the top surface of the base.

An analyte detection system for the detection and measurement of various analytes which are present in a patient's liquid test sample, comprising: a base, the base comprising at least one side, a top surface, and a bottom surface, the base further comprising: a liquid test sample inlet for receiving a patient's liquid test sample, the liquid test sample inlet being located on the top portion of the base; a plurality of microchannels located within the base and in fluid communication with the liquid test sample inlet, the plurality of microchannels being located between the top surface and bottom surface of the base; an electrochemical assay portion; and CO-oximetry assay portion, the CO-oximetry assay portion comprising: a CO-oximetry sensor module, the CO-oximetry sensor module comprising a sample holder configured to hold a volume of the patient's liquid test sample, the sample holder further comprising an optical measurement surface; and wherein the chemical assay portion and the CO-oximetry assay portion are in fluid communication with and connected via the plurality of microchannels.

The analyte detection system, wherein the patient's liquid test sample is whole blood.

The analyte detection system, wherein the volume of whole blood is in a range of from about 40 microliters to about 80 microliters.

The analyte detection system, wherein the various analytes are selected from the group consisting of total hemoglobin, oxyhemoglobin, deoxyhemoglobin, carboxyhemoglobin, methemoglobin, neonatal total bilirubin, and combinations thereof.

The analyte detection system, wherein the detection of the various analytes is accomplished via multi-wavelength spectrophotometry.

The analyte detection system, wherein the analyte detection system is housed in a blood gas analyzer instrument.

The analyte detection system, wherein the CO-oximetry assay portion further comprises a shunt for slicing the patient's liquid test sample to a predetermined thickness.

The analyte detection system, wherein the predetermined thickness is in a range of from about 80 microns to about 160 microns.

A method for detecting the and measuring the presence of various analytes of interest present in a patient's liquid test sample, the method comprising the steps of: obtaining a volume of a patient's liquid test sample in a sample collection device; introducing the patient's liquid test sample from the sample collection device into an analyte detection system, the analyte detection system comprising: a base, the base comprising at least one side, a top surface, and a bottom surface, the base further comprising: a liquid test sample inlet for receiving a patient's liquid test sample, the liquid test sample inlet being located on the top portion of the base; a plurality of microchannels located within the base and in fluid communication with the liquid test sample inlet, the plurality of microchannels being located between the top surface and bottom surface of the base; an electrochemical assay portion; and a CO-oximetry assay portion, the CO-oximetry assay portion comprising: a CO-oximetry sensor module, the CO-oximetry sensor module comprising a sample holder configured to hold a volume of the patient's liquid test sample, the sample holder further comprising an optical measurement surface, wherein the electrochemical assay portion and the CO-oximetry assay portion are in fluid communication with and connected via the plurality of microchannels; interrogating the patient's liquid test sample contained within the sample holder of the CO-oximetry sensor module with at least one wavelength of light; measuring the absorbance of the at least one wavelength of light by the patient's liquid test sample; and calculating corresponding concentrations of the analytes of interest present in the patient's liquid test sample.

The method, wherein the patient's liquid test sample is whole blood.

The method, wherein the volume of whole blood is in a range of from about 40 microliters to about 80 microliters.

The method, wherein the sample collection device is selected from the group consisting of a capillary, vacutainer, and syringe.

The method, wherein the various analytes of interest are selected from the group consisting of total hemoglobin, oxyhemoglobin, deoxyhemoglobin, carboxyhemoglobin, methemoglobin, neonatal total bilirubin, and combinations thereof.

The method, wherein the absorbance is measured via multi-wavelength spectrophotometry.

The method, wherein the analyte detection system is housed in a blood gas analyzer instrument.

The method, wherein the optical cell and the sensor module are formed within and located on the top surface of the base.

Thus, in accordance with the presently disclosed and claimed inventive concept(s), there have been provided systems, devices, and methods related to the use(s) of an improved CO-oximetric slide cell system within a blood gas analyzer for the detection of blood gases and hemoglobin species present within a patient's liquid test sample. As described herein, the presently disclosed and claimed inventive concept(s) relate to embodiments of an improved CO-oximetric slide cell system within a blood gas analyzer, the improved system comprising and/or consisting of at least one CO-oximetry slide cell that is formed as a unitary structure(s) with (i.e., not separately connected to) a CO-oximetry sensor module. Such presently disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. An analyte detection system for the detection and measurement of various analytes which are present in a patient's liquid test sample, comprising:
   a base, the base comprising at least one side, a top surface, and a bottom surface, the base further comprising:
      a liquid test sample inlet for receiving a patient's liquid test sample, the liquid test sample inlet being located on the top surface of the base;
      a plurality of microchannels located within the base and in fluid communication with the liquid test sample inlet, the plurality of microchannels being located between the top surface and bottom surface of the base;
   an electrochemical assay portion; and
   a CO-oximetry assay portion, the CO-oximetry assay portion comprising:
      a CO-oximetry sensor module, the CO-oximetry sensor module comprising a sample holder configured to hold a volume of the patient's liquid test sample, the sample holder further comprising an optical measurement surface;
      a shunt configured to engage the patient's liquid test sample within the sample holder, wherein the shunt is configured to move longitudinally to deposit a predetermined thickness of the patient's liquid test sample on the optical measurement surface, wherein the predetermined thickness is in a range of from about 80 microns to about 160 microns; and
      wherein the CO-oximetry sensor module further comprises an actuator for operating the shunt; and
   wherein the electrochemical assay portion and the CO-oximetry assay portion are in fluid communication with and connected via the plurality of microchannels.

2. The analyte detection system of claim 1, wherein the patient's liquid test sample is whole blood.

3. The analyte detection system of claim 2, wherein the volume of whole blood is in a range of from about 40 microliters to about 80 microliters.

4. The analyte detection system of claim 1, wherein the various analytes are selected from the group consisting of total hemoglobin, oxyhemoglobin, deoxyhemoglobin, carboxyhemoglobin, methemoglobin, neonatal total bilirubin, and combinations thereof.

5. The analyte detection system of claim 1, wherein the detection of the various analytes is accomplished via multi-wavelength spectrophotometry, wherein the optical measurement surface of the sample holder of the CO-oximetry sensor module is configured for interrogation by multiple wavelengths of light.

6. The analyte detection system of claim 1, wherein the analyte detection system is housed in a blood gas analyzer instrument.

7. A method for detecting and measuring the presence of various analytes of interest present in a patient's liquid test sample, the method comprising the steps of:
obtaining a volume of a patient's liquid test sample in a sample collection device;
introducing the patient's liquid test sample from the sample collection device into an analyte detection system, the analyte detection system comprising:
a base, the base comprising at least one side, a top surface, and a bottom surface, the base further comprising:
a liquid test sample inlet for receiving a patient's liquid test sample, the liquid test sample inlet being located on the top surface of the base;
a plurality of microchannels located within the base and in fluid communication with the liquid test sample inlet, the plurality of microchannels being located between the top surface and bottom surface of the base;
an electrochemical assay portion; and
a CO-oximetry assay portion, the CO-oximetry assay portion comprising:
a CO-oximetry sensor module, the CO-oximetry sensor module comprising a sample holder configured to hold a volume of the patient's liquid test sample, the sample holder further comprising an optical measurement surface,
a shunt which engages the patient's liquid test sample within the sample holder, wherein the shunt moves in a longitudinal direction and deposits a predetermined thickness of the patient's liquid test sample on the optical measurement surface, wherein the predetermined thickness is in a range of from about 80 microns to about 160 microns; and
wherein the CO-oximetry sensor module further comprises an actuator for operating the shunt; and
wherein the electrochemical assay portion and the CO-oximetry assay portion are in fluid communication with and connected via the plurality of microchannels;
interrogating the patient's liquid test sample contained within the sample holder of the CO-oximetry sensor module with at least one wavelength of light;
measuring the absorbance of the at least one wavelength of light by the patient's liquid test sample; and
calculating corresponding concentrations of the analytes of interest present in the patient's liquid test sample.

8. The method of claim 7, wherein the patient's liquid test sample is whole blood.

9. The method of claim 7, wherein the volume of whole blood is in a range of from about 40 microliters to about 80 microliters.

10. The method of claim 7, wherein the sample collection device is selected from the group consisting of a capillary, vacutainer, and syringe.

11. The method of claim 7, wherein the various analytes of interest are selected from the group consisting of total hemoglobin, oxyhemoglobin, deoxyhemoglobin, carboxyhemoglobin, methemoglobin, neonatal total bilirubin, and combinations thereof.

12. The method of claim 7, wherein the absorbance is measured via multi-wavelength spectrophotometry.

13. The method of claim 7, wherein the analyte detection system is housed in a blood gas analyzer instrument.

14. The method of claim 7, wherein the electrochemical assay portion and the CO-oximetry sensor module are formed within and located on the top surface of the base.

* * * * *